United States Patent
Glass (10) Patent No.: US 10,192,193 B1
(45) Date of Patent: Jan. 29, 2019

(54) SYSTEMS AND METHODS FOR IMPROVING CENTRAL PHARMACY-TYPE DISPENSING OPERATIONS

(75) Inventor: Larry Glass, Ferndale, CA (US)

(73) Assignee: McKesson Specialty Care Distribution Corporation, San Francisco, CA (US)

( * ) Notice: Subject to any disclaimer, the term of this patent is extended or adjusted under 35 U.S.C. 154(b) by 460 days.

(21) Appl. No.: 13/536,444

(22) Filed: Jun. 28, 2012

(51) Int. Cl.
G06F 19/00 (2018.01)
G06Q 10/08 (2012.01)
G06Q 50/22 (2018.01)

(52) U.S. Cl.
CPC .......... G06Q 10/087 (2013.01); G06F 19/00 (2013.01); G06Q 50/22 (2013.01)

(58) Field of Classification Search
CPC ...... G06Q 50/22; G06Q 10/087; G06F 19/00; G06F 19/3456
USPC ........................................................ 705/2–3
See application file for complete search history.

(56) References Cited

U.S. PATENT DOCUMENTS

| | | |
|---|---|---|
| 5,628,530 A | 5/1997 | Thornton |
| 6,012,035 A | 1/2000 | Freeman et al. |
| 6,757,898 B1 | 6/2004 | Ilsen et al. |
| 6,769,228 B1 | 8/2004 | Mahar |
| 6,889,231 B1 | 5/2005 | Souder |
| 7,031,974 B1 | 4/2006 | Subramanium |
| 7,058,584 B2 | 6/2006 | Kosinski et al. |
| 7,155,397 B2 | 12/2006 | Alexander et al. |
| 7,702,525 B2 | 4/2010 | Kosinski et al. |
| 2002/0002495 A1 | 1/2002 | Ullman |
| 2002/0052760 A1 | 5/2002 | Munoz et al. |
| 2002/0087583 A1 | 7/2002 | Morgan et al. |
| 2002/0111832 A1 | 8/2002 | Judge |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0039599 A1 | 2/2004 | Fralic |
| 2004/0073457 A1 | 4/2004 | Kalies |
| 2004/0078234 A1 | 4/2004 | Joseph, Jr. |

(Continued)

FOREIGN PATENT DOCUMENTS

| | | |
|---|---|---|
| CA | 2482370 | 3/2006 |
| WO | 1995003569 | 2/1995 |

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Joy Chng
(74) *Attorney, Agent, or Firm* — Ballard Spahr LLP (57) ABSTRACT

Systems and methods for improving central pharmacy-type dispensing operations. In one embodiment, a method can include receiving medication order data associated with one or more patients, generating an order worklist based at least in part on the medication order data, creating one or more medication dispensing queues based at least in part on the order worklist, and facilitating output of at least one or more medication dispensing queues for presentation to a pharmacy.

12 Claims, 7 Drawing Sheets

(56) References Cited

U.S. PATENT DOCUMENTS

| | | |
|---|---|---|
| 2004/0117323 A1 | 6/2004 | Mindala |
| 2004/0148198 A1 | 7/2004 | Kalies |
| 2004/0193653 A1 | 9/2004 | Howard |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0080651 A1* | 4/2005 | Morrison ............. G06Q 10/087 705/2 |
| 2005/0086081 A1 | 4/2005 | Brock-Fisher |
| 2005/0102169 A1 | 5/2005 | Wilson |
| 2005/0182656 A1 | 8/2005 | Morey |
| 2005/0187793 A1 | 8/2005 | Myles |
| 2005/0193041 A1 | 9/2005 | Bourbonnais |
| 2005/0197862 A1 | 9/2005 | Paterson et al. |
| 2005/0210114 A1 | 9/2005 | Washburn |
| 2005/0240473 A1 | 10/2005 | Ayers, Jr. et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0116905 A1 | 6/2006 | Yared |
| 2006/0149784 A1 | 7/2006 | Tholl et al. |
| 2006/0184391 A1 | 8/2006 | Barre et al. |
| 2006/0259363 A1 | 11/2006 | Jhetam et al. |
| 2006/0282289 A1 | 12/2006 | Jacobs et al. |
| 2007/0005402 A1 | 1/2007 | Kennedy et al. |
| 2007/0050209 A1 | 3/2007 | Yered |
| 2007/0088566 A1* | 4/2007 | Berkelhamer ......... G16H 40/20 705/2 |
| 2007/0136100 A1 | 6/2007 | Daugherty et al. |
| 2007/0168228 A1 | 7/2007 | Lawless |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0015897 A1 | 1/2008 | Moradi et al. |
| 2009/0070391 A1 | 3/2009 | Blair |
| 2009/0287350 A1* | 11/2009 | Johnson ............. G06F 19/3462 700/236 |
| 2010/0022231 A1 | 1/2010 | Heins et al. |
| 2010/0070298 A1 | 3/2010 | Kalies |
| 2010/0082367 A1 | 4/2010 | Hains et al. |
| 2011/0084135 A1* | 4/2011 | Philippe ............... G06Q 10/087 235/385 |
| 2012/0205441 A1* | 8/2012 | Utech ................... G06Q 50/22 235/376 |
| 2014/0052690 A1 | 2/2014 | Kamireddy |

FOREIGN PATENT DOCUMENTS

| | | |
|---|---|---|
| WO | 2000039737 | 7/2000 |
| WO | 2007025295 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Eitan Blumin, Service broker sample: Asynchronous Triggers, Dec. 4, 2013. pp. 1-20.

Gmatteson, SQL Server 2012. Update second table based on input from first table, Nov. 19, 2013. pp. 1-2.

Non-Final Office Action for U.S. Appl. No. 14/674,366 dated Apr. 11, 2016.

Final Office Action for U.S. Appl. No. 14/674,366 dated Oct. 13, 2016.

* cited by examiner

Dispense – Select Patient

Patient Name: [____] ID: [____] DOB: [____] 🗓
mm/dd/yyyy

Patient Search Results

| Patient Name | Sex | ID | Birthdate |
|---|---|---|---|
| 502 | | | |

Patients in Queue

| Patient Name | Sex | ID | Birthdate |
|---|---|---|---|
| Name not shown for patient confidentiality – [Queue] | F | zztest2 | 1/1/1980 [Update History] |
| Name not shown for patient confidentiality – [Queue] | F | zztest1 | 1/1/1980 [Update History] |
| Name not shown for patient confidentiality – [Queue] | F | humpdy1 | 1/1/1950 [Update History] |
| 504 | | | |

Patients Dispensed Today

| Patient Name | Sex | ID | Birthdate |
|---|---|---|---|
| 506 | | | |

Patients Scheduled for Today

| Patient Name | Sex | ID | Birthdate |
|---|---|---|---|
| 508 | | | |

Patients with Orders for Today

| Patient Name | Sex | ID | Birthdate |
|---|---|---|---|
| Name not shown for patient confidentiality – [Queue] | | 240480 | |
| Name not shown for patient confidentiality – [Queue] | | 211426 | |
| Name not shown for patient confidentiality – [Queue] | | 218493 | |

CALENDAR 510
Filters
FILTERS 512

Dispense -- Add Items
Select items from the History, Treatment Regimen, and/or Inventory menu
Patient: -- Name not shown for patient confidentiality --

| | | | | |
|---|---|---|---|---|
| DOB: | 12/12/1901 | Height: 62 in | Diagnosis: | 153.9 -- Malignant NEO COLON NOS, Stage: III |
| ID: | 1342 | Weight: 156 lbs | | 285.9 -- Anemia NOS, Stage: |
| Physician: | Amy, Lee | | | |
| Allergies: | Drugs | | | |
| Note: | | | | |

[RETURN TO SEARCH]

| History | Treatment Regimen | Items |

Name (Brand or Code): g-c

| | | Previous 1 Next | | |
|---|---|---|---|---|
| | | | Inv Qty | Partial |
| ⊕ | G-Csf 300 mcg Syringe 10 per Box -- Neupogen 300 mcg Syringe 10 per Box (55513-0924-10) | | 16 Syringe | 1 mcg |
| ⊕ | G-Csf 480 mcg Syringe 10 per Box -- Neupogen 480 mcg Syringe 10 per Box (55513-0209-10) | | 6 Syringe | 479 mcg |
| ⊕ | G-Csf Sol 300 mcg per 1mL -- Neupogen 0.3 mg per mL 1 mL (55513-0530-10) | | 0 Vial | 0 mcg |

MULTI-SELECT CALENDAR MODULE 604

Date of Service: [<<PREV] [NEXT>>] Clinical Trial: None ▾ New

CALENDAR 602

✗ DEL ALL

| | Name (Brand or Code) | Disp Amt | Inv Amt | Waste | Total | Inv Qty | Partial |
|---|---|---|---|---|---|---|---|
| ✗ | G-Csf 480 mcg Syringe 10 per Box -- Neupogen 480 mcg Syringe 10 per Box (55513-0209-10) [Instructions] | [ ] mcg | 1 Syringe | ☐ 0 mcg | 480 mcg | 6 Syr | 479 mcg |

[Queue]

SELECTION MODULE 606

SYSTEMS AND METHODS FOR IMPROVING CENTRAL PHARMACY-TYPE DISPENSING OPERATIONS

FIELD OF THE DISCLOSURE

Aspects of the disclosure relate generally to the dispensing of healthcare products and services, and more particularly, to improving central pharmacy-type dispensing operations.

BACKGROUND

Some conventional healthcare treatment facilities utilize a single pharmacy operation (referred to herein as a "central pharmacy") to prepare treatment regimens and/or services to be performed in multiple physical office or treatment locations. Often, central pharmacy operations utilize a conventional single clinic pharmacy workflow model to gather patient information and dispense patient medication. The single clinic workflow model is typically designed to satisfy a particular patient encounter and fails to efficiently serve multiple office locations and and/or high patient volumes.

BRIEF DESCRIPTION

Some or all of the above needs and/or problems may be addressed by certain embodiments of the disclosure. Embodiments of the disclosure may include systems and methods for improving central pharmacy-type dispensing operations. Certain embodiments of the disclosure can include systems and methods for requesting data associated with one or more patients, creating an order worklist associated with the patient data, and/or generating one or more dispensing queues from the order worklist.

In one embodiment, a method for improving central pharmacy-type operations can be provided. The method can include receiving medication data associated with one or more patients. The method can also include generating an order worklist based at least in part on the medication order data. Furthermore, the method can include creating one or more medication dispensing queues based at least in part on the order worklist, wherein each medication dispensing queue includes one or more medication order transactions. Moreover, the method can include facilitating output of at least one of the medication dispensing queues for presentation to a pharmacy, wherein the one or more medication order transactions of the at least one medication queue is filled by the pharmacy.

In accordance with another embodiment, a system for improving central pharmacy-type operations can be provided. The system can include at least one memory that stores computer-executable instructions. The system can also include at least one processor configured to access the at least one memory and execute the computer-executable instructions. The computer executable instructions can be configured to receive medication order data from respective electronic health records associated with one or more patients; generate an order worklist based at least in part on the medication order data; create one or more medication dispensing queues based at least in part on the order worklist, wherein each medication dispensing queue includes one or more medication order transactions; and facilitate output of at least one medication dispensing queue for presentation to a pharmacy, wherein the one or more medication order transactions of the at least one medication dispensing queue is filled by the pharmacy.

In accordance with another embodiment, one or more computer-readable media for improving central pharmacy-type operations can be provided. The one or more computer-readable media may include computer-executable instructions that, when executed on one or more processors, cause the one or more processors to perform operations comprising: receiving medication order data from an electronic health records system; creating an order workflow and one or more dispensing queues for dispensing patient medications; wherein the order workflow or the one or more dispensing queues include medication order data filtered according to a specific patient, a date and/or a date range, a medication and/or combination of medications, and/or a treatment location.

Additional systems, methods, computer-readable media, features, and aspects may be realized through the techniques of various embodiments of the disclosure. Other embodiments and aspects of the disclosure are described in detail herein with reference to the description and to the drawings and are considered a part of the claimed invention.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Overview

The present disclosure relates to systems and methods for improving central pharmacy-type operations. In an example embodiment, a pharmacy professional (referred to herein as a "pharmacist") may query an electronic health record ("EHR") system to obtain medication order data from respective electronic health records stored in the EHR system. In some instances, the medication order data may be filtered to obtain a discrete set of medication order data. For example, the pharmacist may utilize at least one filter using criteria, such as a specific treatment location, a medication type, a date and/or a date range of treatments, etc. The filtered medication order data may be presented to the pharmacist as an order worklist via a graphical user interface output on an electronic display. Using the order worklist, the pharmacist can readily view medication order transactions associated with certain medical order data, and can begin filling some or all of the medical order transactions as needed. The pharmacist can interact with the order worklist as needed to edit, delete, or modify medical order transaction data, and track any number of medical order transactions.

In one example embodiment, the pharmacist may work through the order worklist to generate one or more medication dispensing queues. The medication dispensing queues can be configured to be output via a graphical user interface on an electronic display. The one or more medication dispensing queues may be filtered using criteria such as medication type, medication storage location, treatment location, a date and/or a date range of treatments, etc. In some instances, the one or more medication dispensing queues can be generated by the pharmacist's selection of certain medication order data or medication order transactions. The pharmacist selection may include, without limitation, determining each medication to be used by each patient and processing the medication to the one or more dispensing queues. In some instances, medications corresponding to multiple dispensing dates may be processed accordingly, resulting in multiple entries in the one or more dispensing queues corresponding to multiple dates. In one non-limiting example, the one or more dispensing queues may be generated without requiring the pharmacist to navigate away from the order workflow.

In some instances, a printout of the one or more dispensing queues may be generated by a practice management module and supplied to a pharmacist. For example, the pharmacist, may receive a printout from a physicians office including, without limitation, patient information associated with medication orders for a specific date and/or date range as well as medication orders associated with treatment facilities. In some instances, the pharmacist may utilize an order selection module to process the patient information for each individual entry contained on the printout to generate the one or more dispensing queues.

The one or more dispensing queues may be filtered to coincide with a pharmacies desired workflow. For example, the workflow may be organized according to medication location within the pharmacy, thereby establishing a more efficient workflow for dispensing medication and completing treatment orders for multiple patients. In another example, the one or more dispensing queues may be filtered to meet the requirements of many desired pharmacy workflows.

The following discussion begins with a section entitled "Illustrative Architecture," which describes an example central pharmacy-type dispensing operation system according to an embodiment of the disclosure. The discussion continues with section entitled "Illustrative Processes", and then concludes with a section entitled "Illustrative Graphical User Interfaces.".

This brief introduction, including section titles and corresponding summaries, is provided for the reader's convenience and is not intended to limit the scope of the claims, nor the proceeding sections. Furthermore, the techniques described above and below may be implemented in a number of ways and in a number of contexts. Several example implementations and contexts are provided with reference to the following figures, as described below in more detail. However, the following implementations and contexts are but a few of many.

Embodiments of the disclosure now will be described more fully hereinafter with reference to the accompanying drawings, in which embodiments of the disclosure are shown. The foregoing ideas may, however, be embodied in many different forms and should not be construed as limited to the embodiments set forth herein; rather, these embodiments are provided so that this disclosure will be thorough and complete, and will fully convey the scope of the disclosure to those skilled in the art. Like numbers refer to like elements throughout.

Illustrative Architecture

Figure 1:
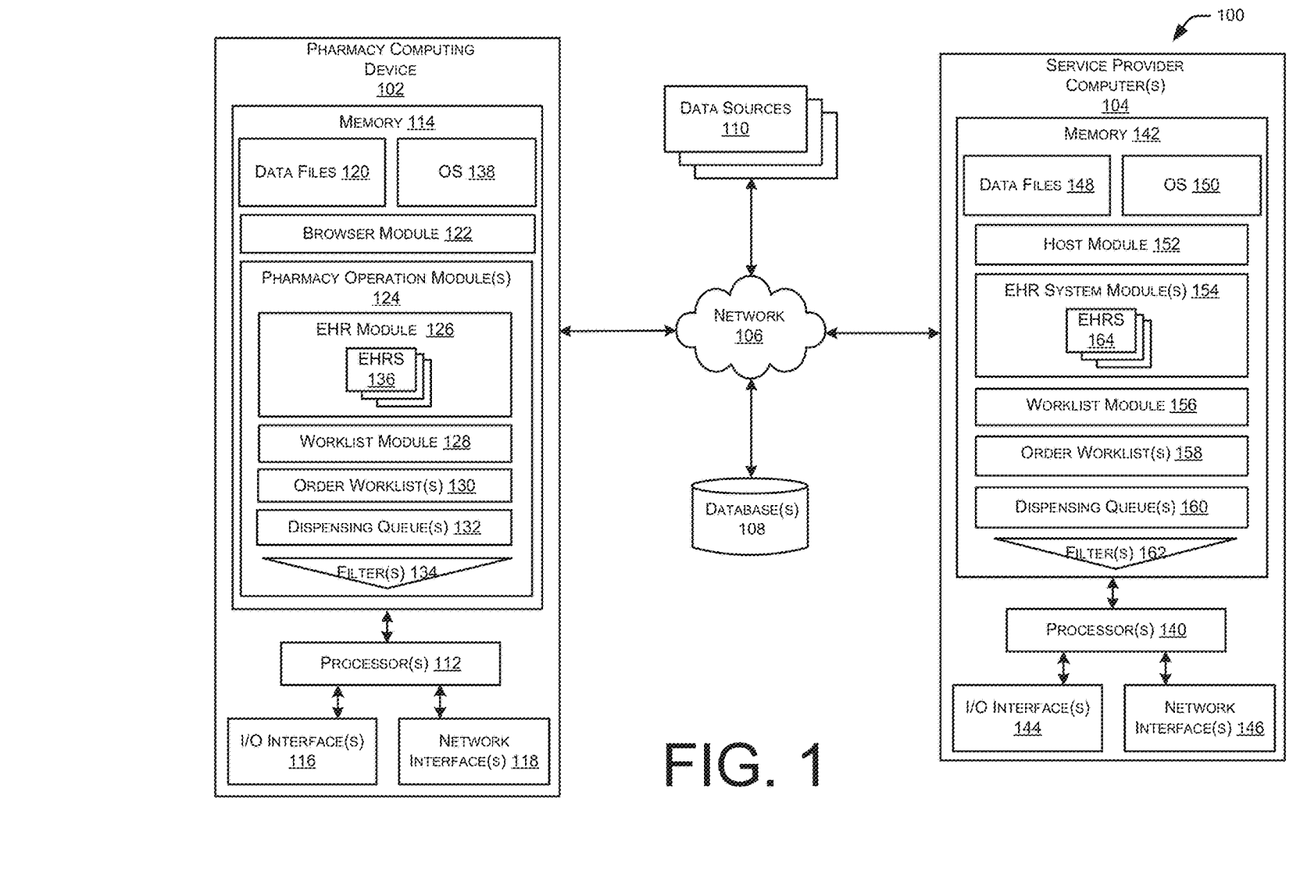
FIG. 1 illustrates an example block diagram of an example system for improving central pharmacy-type operations according to an embodiment of the disclosure.

FIG. 1 depicts an illustrative environment and system 100 in which techniques for providing improved central pharmacy-type dispensing operations may be implemented. As shown in FIG. 1, the system 100 may include at least one pharmacy computing device 102 and one or more service provider computers 104 in communication via a network 106. In the embodiment shown in FIG. 1, a pharmacy computing device 102 can be associated with a pharmacist or other healthcare professional. Further, the one or more service provider computers 104 can host an electronic health record (EHR) system, such as hosting an EHR system module or application program. For example, the pharmacy computing device 102 may be configured to receive a pharmacist input or instruction to obtain medication order data from one or more electronic health records stored in an EHR. The medication order data may be communicated to the computing device from one or more service provider computers 104 hosting or otherwise facilitating access to the electronic health records and EHR or EHR system module or application program.

Even though an individual pharmacy computing device 102 is shown in FIG. 1, any number of pharmacy computing devices, such as 102, may be implemented in embodiments of the system 100. Further, even though the pharmacy computing device 102 can be associated with a pharmacist, the device 102 is not limited to being located at or operated within a pharmacy. In the embodiment shown in FIG. 1, a pharmacy computing device 102 may be a desktop computer, laptop computer, mobile terminal, mobile communication device, processor-based device, and/or any combination thereof. In embodiments wherein the pharmacy computing device 102 comprises multiple computing devices, the multiple computing devices may be in communication with each other, such as over the network 106 to collectively perform one or more functionalities of the pharmacy computing device 102 as described herein. Further, even though an individual service provider computer 104 is shown in FIG. 1, any number of service provider computing devices can be implemented in embodiments of the system 100. In embodiments where the service computer device 104 comprises multiple service computer devices, the multiple service computer devices 104 may be in communication with each other, such as over the network 106 to collectively perform one or more functionalities of the service computer devices 104 as described herein.

According to an example embodiment, the system 100 may additionally include, without limitation, one or more databases 108 and one or more data sources 110, each accessible by the pharmacy computing device 102 and/or the one or more service provider computers 104. As desired, the network 106 may facilitate communication between various components of the system 100. Additionally, as desired, the pharmacy computing device 102, the one or more service provider computers 104, the one or more databases 108, and the one or more data sources 110 may include one or more processing devices that may be configured for accessing and reading associated computer-readable media having data stored thereon and/or computer-executable instructions for implementing the various processes or methods of the disclosure.

In some instances, the one or more databases 108 may include, without limitation, internal databases stored by the pharmacy computing device 102 and/or the service provider computers 104. Additionally and/or alternatively, the one or more databases 108 may include external or remote databases accessible via the network 106. The one or more databases 108 may be configured to store a wide variety of information that may be accessed and evaluated during the processing of the pharmacist input or instruction to obtain medication order data from one or more electronic health records stored in an EHR, including, without limitation, structured healthcare information, medical order data, patient information (e.g., a patient's medical record), healthcare provider information, and/or information that may be utilized to generate any of the prior described information.

Generally, in certain aspects, the pharmacy computing device 102, the one or more service provider computers 104, the one or more databases 108, and/or the one or more data sources 110 may include or otherwise be associated with suitable hardware and/or software for transmitting and receiving data, signals, and/or computer-executable instructions over one or more communications links or networks. As desired, any number of processors for processing data and executing computer-executable instructions, as well as other internal and peripheral components that are well-known in the art, may be implemented by these example system components. In some instances, the computing device 102 and/or the service provider computers 104 may function as data sources.

Further, these example system components may include or be in communication with any number of suitable memory devices operable to store data and/or computer-executable instructions. By executing computer-executable instructions, each of the example system components may form a special purpose computer or particular machine. As used herein, the term "computer-readable medium" describes any form of suitable memory or memory device.

As illustrated in FIG. 1, the pharmacy computing device 102, the one or more service provider computers 104, the one or more databases 108, and/or the one or more data sources 110 may be in communication with each other via the network 106. The network 106 is referred to in the singular form herein, but in certain embodiments, the network 106 may comprise any number of networks in communication with each other, including any number of wireless or wired networks. The network 106 may include, without limitation, any number of telecommunication and/or data networks, whether public, private, or a combination thereof, including a local area network, a public switched telephone network, a wide are network a cellular network, an intranet, the Internet, intermediate handheld data transfer devices, and/or any combination thereof and may be wired and/or wireless. Due to network connectivity, various methodologies as described herein may be practiced in the context of distributed computing environments. It is to be understood that any other network configuration is possible. For example, a network 106 may include a plurality of networks, each with devices such as gateways and routers for providing connectivity between or among networks. Instead of or in addition to a network 106, dedicated communication links may be used to connect the various devices in accordance with an example embodiment of the disclosure.

In the example configuration shown in FIG. 1, the pharmacy computing device 102 can include, without limitation, one or more processors 112, a memory 114, one or more input/output (I/O) interfaces 116, and/or one or more network interfaces 118. The memory 114 may include any suitable memory, for example, caches, read-only memory, random access memory, magnetic storage devices, removable storage devices, etc. The memory 114 may store data, executable instructions, and/or various program modules utilized by the pharmacy computing device 102, such as, for example, one or more data files 120, a browser module 122, and/or one or more pharmacy operation modules 124. In some instances, the one or more data files 120 may include any suitable data that facilitates the communication with the service provider computers 104, and/or the one or more databases 108, and/or the one or more data sources 110. For example, the data files 120 may include, without limitation, identification information for other components of the system 100, information that facilitates the establishment of communication sessions and/or other communication with other components of the system 100, and/or database management information.

In some instances, I/O interfaces 116 may facilitate communication between the pharmacy computing device 102 and the one or more associated I/O devices, such as, for example, one or more user interfaces including, without limitation, a display, a keypad, a control panel, a touch screen display, a remote control, a microphone, a speaker, a gesture control device, a stylus, a mouse, etc., that facilitate user interaction with the pharmacy computing device 102. For example, the computing device 102 may receive and/or communicate pharmacist or healthcare professional input or instructions to other system components, such as one or more service provider computers 104, one or more databases 108, and/or one or more data sources 110.

As described above, the memory 114 of the pharmacy computing device 102 may be configured to store applications and data, such as, without limitation, the browser module 122 and the pharmacy operation module(s) 124. In some instances the browser module 122 may be an Internet browser or other software, including a dedicated program or application program, for interacting with the one or more service provider computers 104, one or more databases 108, and/or one or more data sources 110. In one example operation, a user, such as a pharmacist or healthcare professional, may utilize the browser module 122 to establish a communications session with the one or more service provider computers 104. It is to be appreciated that the physician or healthcare professional may access one or more service provider computers 104 remotely via the browser module 122 using, for example, a private login and password associated with the physician or healthcare professional.

With continued reference to FIG. 1, in some instances, the one or more pharmacy operation modules 124 may include an EHR module 126, a worklist module 128, one or more order worklists 130, one or more dispensing queues 132, one or more filters 134, and one or more electronic health records (EHRS) 136. The EHR module 126 may include, without limitation, any number of suitable software modules and/or application programs configured to access, via the network 106, one or more service provider computers 104 hosting an hosting an EHR system module or application program. In one non-limiting example, the EHR module 126 may provide user access to, without limitation, one or more patient electronic health records, patient profiles, a medication histories, appointment schedules, physician charts, medication orders, medication order transactions, physician notes, and other information stored in an EHR system module or application program, one or more service provider computers 104, one or more databases 108, and/or one or more data sources 110.

In the embodiment shown in FIG. 1, the EHR module 126 may communicate with a worklist module, such as 128, to generate, obtain, or otherwise receive medication order data from respective electronic health records associated with one or more patients. In turn, the worklist module, such as 128, can communicate, via the network 106, with one or more service provider computers 104 to generate, obtain, or otherwise receive medication order data from respective electronic health records associated with one or more patients. The medication order data and electronic health records are usually stored in or otherwise managed by an EHR system module or application program, such as 146, but could be stored in memory 134 associated with one or more service provider computers 104. In certain embodiments, some or all of the medication order data and electronic health records may be stored in one or more databases 108 and/or one or more data sources 110, from which the worklist module, such as 128, may communicate, via the network 106, to obtain or otherwise receive medication order data from respective electronic health records associated with one or more patients. In certain other embodiments, the EHR module 126 may communicate with a worklist module operating at the one or more service provider computers, such as worklist module 156, to generate, obtain, or otherwise receive medication order data from respective electronic health records associated with one or more patients. In certain other embodiments, functionality can be distributed between two or more worklist modules, such as 128 and 156, to generate, obtain, or otherwise receive medication order data from respective electronic health records associated with one or more patients. In any instance, at least one worklist module, such as 128 and/or 156, can generate, obtain, or otherwise receive medication order data from respective electronic health records associated with one or more patients.

For example, a pharmacist or other healthcare professional can interact with the pharmacy computing device 102 via at least one I/O interface 116, such as a graphical user interface and a touchpad, to input a command to generate, obtain, or otherwise receive medication order data from respective electronic health records associated with one or more patients. The EHR module 126 can instruct the worklist module 128 to communicate with the EHR system module 154 to access medication order data in any number of electronic health records, such as 164, stored by the service provider computers 104, such as in memory 134.

In the embodiment shown in FIG. 1, upon or after generation, obtaining, or receipt of medical order data, the worklist module, such as 128, can generate one or more order worklists 130 based at least in part on the medication order data. The worklist module 128 may facilitate output or the presentation of some or all of the medical order data to the pharmacist using the I/O interface(s) 116. The worklist module 128 may permit the pharmacist to select and review certain individual medical order data or groups of medical order data.

Additionally, the pharmacy computing device 102 may include an operating system 138 that may be a suitable software module that controls the general operation of the pharmacy computing device 102. The operating system 138 may also facilitate the execution of other software modules by the one or more processors 112, such as, for example, the browser module 122, the EHR module 126, and/or the worklist module 128. The operating system may be, without limitation, Microsoft Windows®, Apple OSX™, Linux, Unix, or a mobile operating system.

The pharmacy computing device 102 as described in FIG. 1 is by example only. One will recognize that the pharmacy computing device may not include the pharmacy operation modules 124 (e.g., the EHR module 126, the worklist module 128, the order worklist 130, the dispensing queues 132, the filters 134 and/or the EHRS 136), and may utilize the browser module 122 to access a remote computing device (e.g., service provider 104). The remote computing device may access remote databases (e.g., databases 108 and/or data sources 110) to retrieve EHR data requested by the pharmacy computing device 102 and generate a viewable order worklist. The remote computing device may deliver the viewable order worklist to the pharmacy computing device 102 over the networks 106 for processing by a receiving pharmacist.

In one illustrative configuration, each service provider computer 104 may include, without limitation, any suitable processor-driven device configured for receiving pharmacist input or instructions, processing the received input or instructions, and/or communicating medical order data (e.g., electronic health record data) to the pharmacy computing device 102. In some instances, each service provider computer 104 may include a suitable host server (e.g. a Web server, a server that integrates with dedicated applications on the pharmacy computing device 102, etc.), a host module, or other software that facilitates the receipt and processing of pharmacist input or instructions. Any number of pharmacy computing devices 102 may be in communication with the one or more service provider computers 104.

Each of the service provider computer 104 may include any number of special purpose computers or other particular machines, application-specific circuits, microcontrollers, personal computers, minicomputers, mainframe computers, servers, networked computers, and/or other processor-driven devices. In some instances, the operations of the service provider computers 104 may be controlled by computer-executed or computer-implemented instructions that are executed by one or more processors 140 associated with the service provider computers 104 to form a special purpose computer or other particular machine operable to facilitate receiving and processing physician input. The one or more processors 140 that control the operations of the service provider computers 104 may be incorporated into the service provider computers 104 and/or in communication with the service provider computers 104 via the network 106. In some instances, the operations and/or control of the service provider computers 104 may be distributed among several processing components.

In addition, in some instances the service provider computers 104 may include, without limitation, one or more memory devices 142, one or more input/output (referred to herein as I/O) interfaces 144, and/or one or more network interfaces 146. The memory 142 may be any suitable memory, for example, caches, read-only memory, random access memory, magnetic storage devices, removable memory devices, etc. The memory 142 may store data, executable instructions, and/or various program modules utilized by the service provider computers 104, for example, data files 148, an operating system 150, a host module 146, one or more EHR system modules 154, and a worklist module 156. As desired, the service provider computers 104 may additionally include a suitable database management system configured to manage the data stored in any number of internal and/or external databases, such as databases 108.

The operating system 150 may be a suitable software module that controls the general operation of the service provider computers 104 and/or that facilitates the execution of other software modules. The operating system 150 may be, without limitation, Microsoft Windows®, Apple OSX™, Linux, Unix, or a mainframe operating system. The host module 152 may include any number of suitable modules and/or applications that facilitate communication with the pharmacy computing device 102. In one non-limiting example, the host module 152 may include, without limitation, one or more suitable Web server applications and/or server applications configured to communicate with one or more applications (including dedicated applications) executed by the pharmacy computing device 102. In operation, a host module 152 may receive, process, and/or respond to requests from the pharmacy computing device 102, such as requests to process pharmacist input or instructions. In some instances, the host module 152 may additionally facilitate communications with the databases 108 and/or data sources 110. The EHR system modules 154 may include any number of suitable software modules and/or applications that facilitate the processing of received pharmacist input or instructions, the determination of additional information, and/or the output of the additional information for presentation by the pharmacy computing device 102. In some instances, the EHR system modules 154 may function in a similar manner as the EHR module 126 described above with regards to the pharmacy computing device 102. For example, similar to pharmacy computing device 102, the service provider computers 104 may store module with similar functionality as the EHR module 126 which may include, without limitation, a worklist module 128. The HER system module may be configured to query the one or more service provider computers 104, and/or the one or more databases 108, and/or the one or more data sources 110 to request bulk patient data. In some instances, the bulk patient data may include, without limitation, medication order data from respective electronic health records associated with one or more patients. In some instances, the bulk data may be accessed on the one or more databases 108, one or more data sources 110, and/or the pharmacy computing device 102.

In certain embodiments, one or more filters, such as 134 and 162, may be applied to the bulk data to generate one or more order worklists, such as 130 and 158. In one non-limiting example, an order worklist may be generated after applying one or more filters using certain criteria, such as, a date or a date range, one or more treatment locations, and/or a medication or list of medications. The one or more filters may be implemented by a user, such as a pharmacist or healthcare professional, via a filters link, a popup filter user interface, or other user interface. In some instances, the one or more filters may be applied concurrently. In other instances, the one or more filters may be applied sequentially.

In certain embodiments, an order worklist, such as 130 and 158, may be used to create one or more medication dispensing queues, such as 132 and 160. In one non-limiting example, the one or more medication dispensing queues, such as 132 and 160 may act as an accumulator, accumulating information from a respective order worklist 130 or 158, such as, without limitation, patient names, times and/or dates, medication names, dosage sizes, vial sizes containing dosage, etc. The one or more medication dispensing queues, 132 and 160, may be a dynamic, such that, a medication order transaction within the one or more medication dispensing queues, 132 or 160, may be edited and/or deleted from the respective queue. For example, a medication order transaction may be removed from the one or more dispensing queues, 132 or 160, if a physician changes a medication order for a patient. The service provider computer 104 may be notified of the change by an order change request transmitted to or obtained by the service provider computer 104, and the medication order may be removed from the one or more of the medication dispensing queues, 132 or 160. The pharmacist may re-access the patient's current medication order transactions on the order worklist, such as 130 or 158, and continue with any further processing and/or review.

In some instances, the one or more medication dispensing queues, 132 and 160, may be filtered by a user, such as a pharmacist or healthcare professional, to display an arrangement compatible with the desired pharmacy workflow. For example, the user of the one or more medication dispensing queues, such as 132, may desire an arrangement of the one or more medication dispensing queues 132 according to the physical location of a medication (e.g., door 1, drawer A, etc.) within the pharmacy. Via the I/O interface 116, the user can manipulate the arrangement of the medication dispensing queues 132 on the user interface to the desired arrangement, including, but not limited to, labeling certain portions of the medication dispensing queue 132 consistent with one or more physical locations of any number of medications and/or sequentially ordering certain portions of the medication dispensing queue 132 consistent with the one or more sequential physical locations of any number of medications. In this manner, use of the system 100 can increase the efficiency of the dispensing processes and/or tracking dispensation of the physical products. The example system components and architecture described in FIG. 1 are by example only. Other systems and architectures in accordance with other embodiments of the disclosure can perform some or all of the above-described functionality with fewer or greater numbers of components than shown in FIG. 1. One will recognize that other system architectures can be implemented to achieve some or all of the above-described functionality with respect to FIG. 1.

Illustrative Processes

Figure 2:
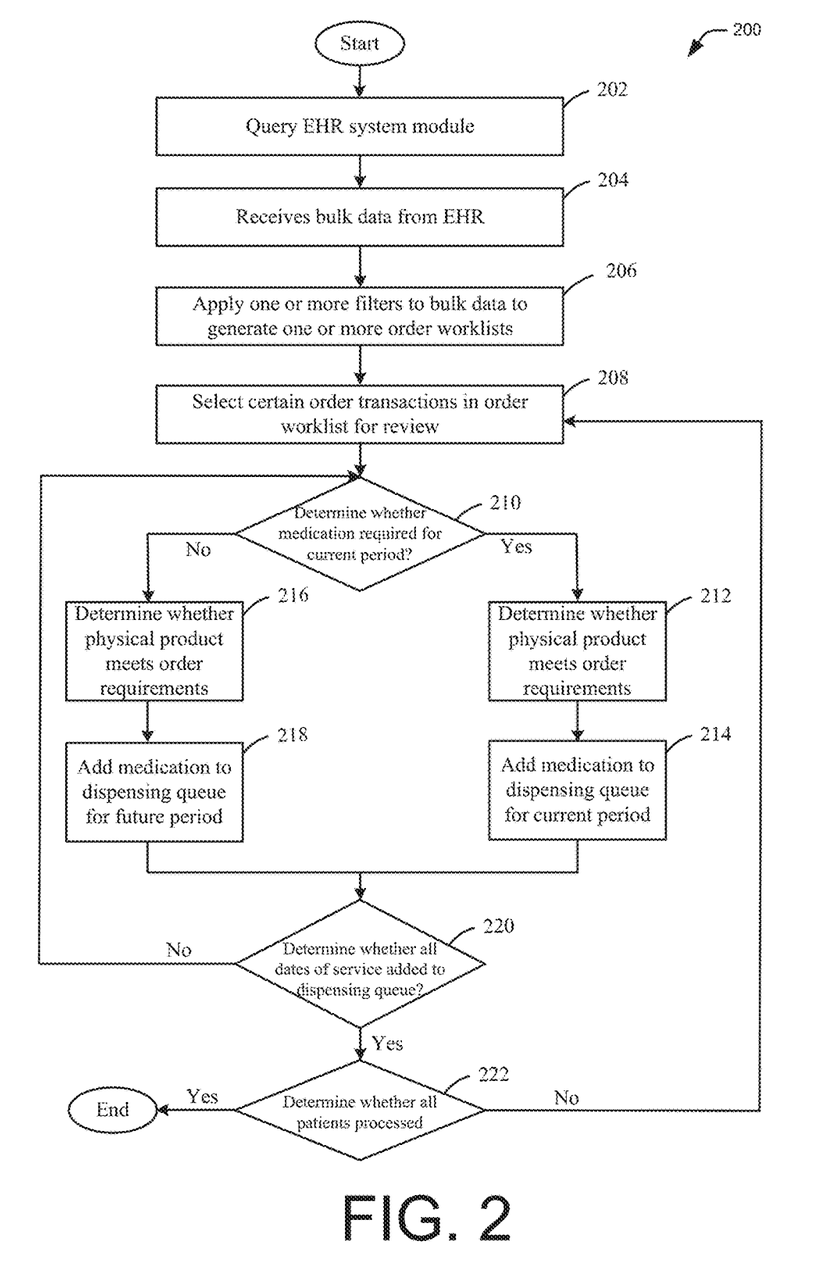
FIG. 2 is a flow diagram of an example method for improving central pharmacy-type operations according to an embodiment of the disclosure.
Figure 3:
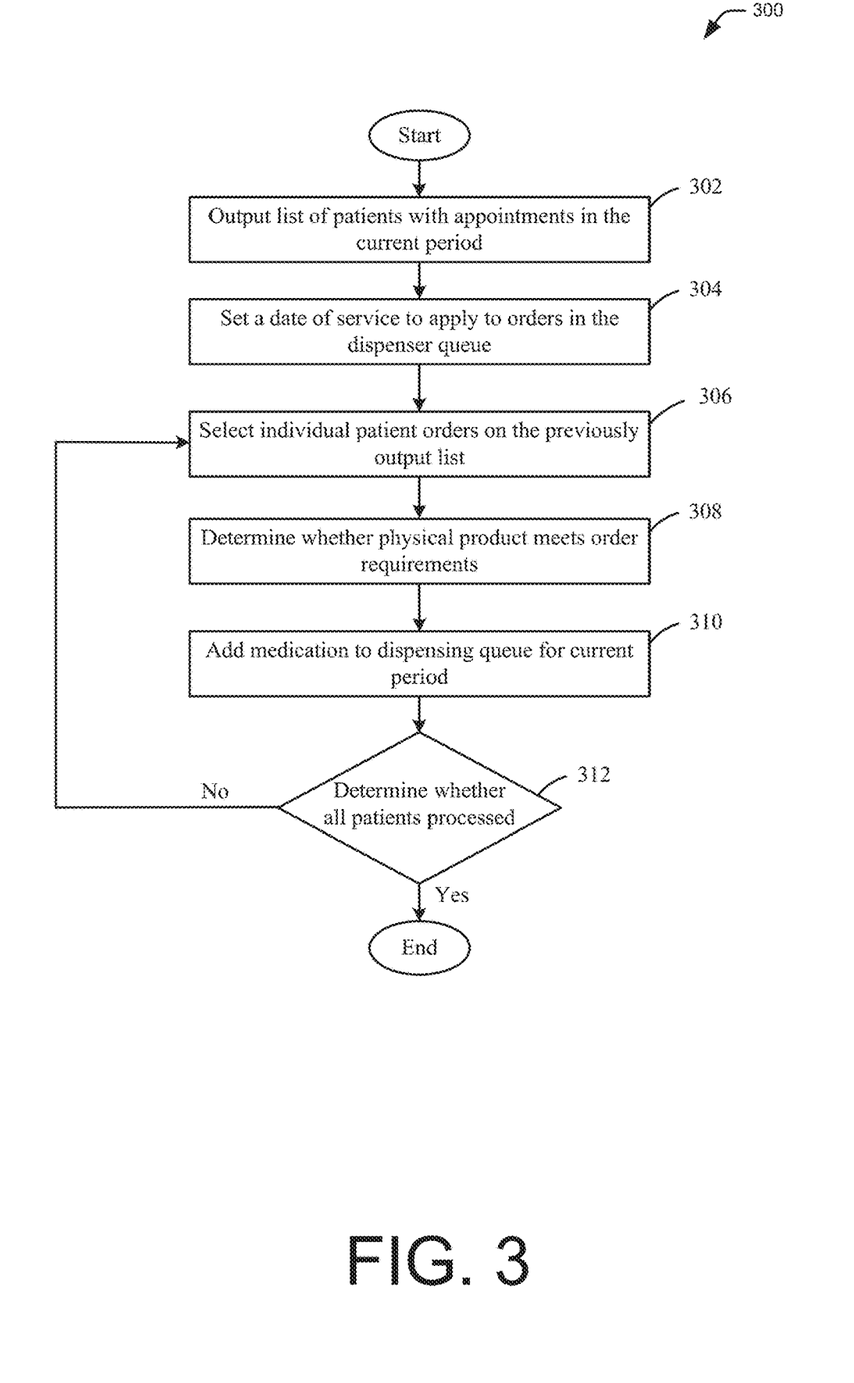
FIG. 3 is a flow diagram of an example method for improving central pharmacy-type operations according to an embodiment of the disclosure.
Figure 4:
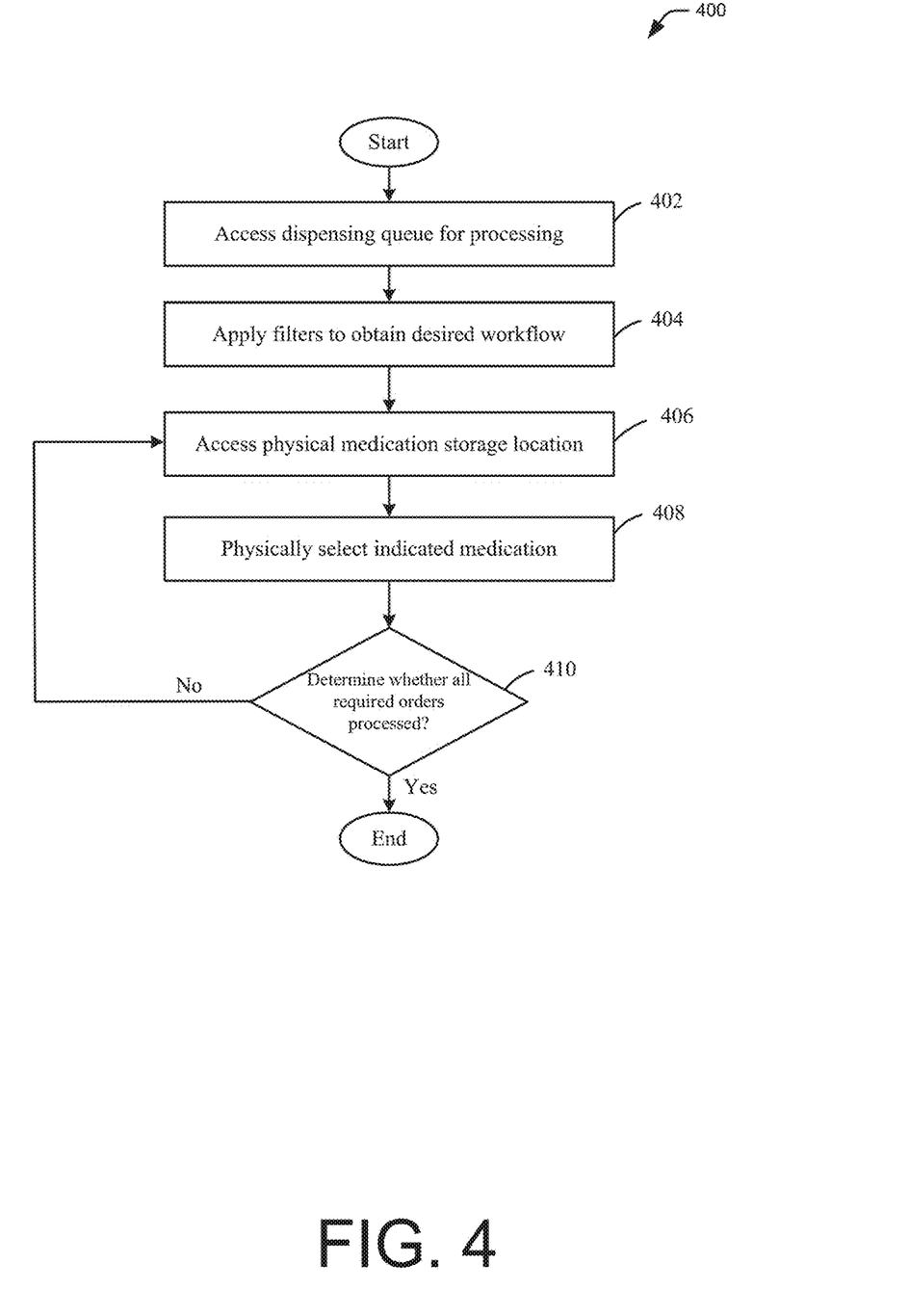
FIG. 4 is a flow diagram of an example method for improving central pharmacy-type operations according to an embodiment of the disclosure.

FIGS. 2-4 illustrate example methods according to embodiments of the disclosure. In certain embodiments, the operations of these example methods may be performed by a pharmacy computing device 102 operating alone, or in conjunction with a service provider computer 104 illustrated in FIG. 1. For example, the operations of these example methods may be performed by an EHR module 126 and worklist module 128 associated with the pharmacy computer 102.

FIG. 2 illustrates a flow diagram of an example method 200 for improving central pharmacy-type dispensing operations according to an embodiment of the disclosure. The method 200 may begin at block 202. At block 202, an EHR module and/or worklist module may be utilized by the pharmacy computer to query an electronic health records ("EHR") system, such as an EHR system module to generate, obtain, or receive bulk patient data including, without limitation, medication order data and patient treatment information such as, a treatment date, one or more medications ordered, a treatment location, etc. In some instances, the bulk patient data may be accessed from one or more databases 108, data sources 110, the pharmacy computing device 102, and/or the service provider computers 104. For example, a pharmacist can utilize an I/O device 116 associated with a pharmacy computing device 102 to input an instruction, such as a query for certain medical order data via a user interface output at the pharmacy computing device 102.

At block 204, the bulk data associated with one or more patients and existing medication orders is received. For example, the pharmacy computing device 102 can receive medical order data in response to the pharmacist's initial query.

At block 206, one or more filters may be applied to the bulk data to generate one or more order worklists. In one non-limiting example, an order worklist may be generated after applying one or more filters including, without limitation, a patient filter, a date or a date range filter, a one or more treatment locations filter, and/or a medication or medications filter. The one or more filters may be launched from a user interface using a filters link, or by invoking a popup filter user interface. The one or more filters may be selected concurrently or sequentially. For example, the pharmacist can select one or more filters from a user interface to apply to the received medical order data in the order worklist.

At block 208, certain medication order transactions in the order worklist can be selected for review. For example, the pharmacist may navigate within the filtered order worklist to select individual patients on the order worklist to process any and all treatment orders associated with the selected patient. The pharmacist may review one or more patient orders associated with the selected patient via the worklist module 130.

At block 210, a determination whether medication is required for the current period is made. For example, the pharmacist may determine a treatment date and/or treatment dates associated with an order or order location for the selected patient. In one non-limiting example, the treatment date may be equivalent to the date the pharmacist processes the order worklist. Alternatively and/or additionally, the treatment date may be a different date than the date the pharmacist processes the order worklist. For example, the pharmacist may navigate the order worklist on Jun. 23, 2012, and the treatment order date may be for Jun. 24, 2012, Jun. 25, 2012, or any future date. If the treatment date ordered corresponds to the date the pharmacist processed the order workflow (referred to herein as the "current date"), method 200 may proceed to block 212. If the treatment date ordered corresponds to a future date, the method 200 may proceed to block 216, discussed below. In some instances, the pharmacist may continue the method, without navigating away from the order worklist.

At block 212, a selection of the appropriate physical product is made according to the order requirements. For example, the pharmacist may determine and/or select an appropriate physical medication product (e.g., medication type(s), size, medication lot, medication compositions, etc.) to fulfill the treatment order for the patient selected from the order workflow. At block 214, the pharmacist may add the treatment order, along with any necessary corresponding patient information to one or more dispensing queues 132, 160 for the current date. In some instances, the pharmacist may add the order to the one or more dispensing queues without navigating away from the order worklist. For example, the pharmacist may work through the order workflow patient by patient, adding medication orders to the one or more dispensing queues 132, 160 without requiring the pharmacist to view the one or more dispensing queues during the process. The method 200 may proceed from block 214 to block 220.

If at block 210, described above, the order date was determined to be a future date, the method 200 continues at block 216. At block 216, a selection of the appropriate physical product is made according to the order requirements. For example, the pharmacist may determine and/or select an appropriate physical medication product (e.g., medication type(s), size, medication lot, medication compositions, etc.) to fulfill the treatment order for the patient selected from the order workflow. At block 218, the pharmacist may add the treatment order, along with any necessary corresponding patient information to one or more dispensing queues 132, 160 for a future date.

At block 220, a determination is made whether the treatment dates for the selected patient includes more than one date of service. For example, the pharmacist may determine, from the order workflow information corresponding to a specific patient, if the treatment order for the selected patient includes more than one date of service. In some instances a treatment may require more than one separate dispensing dates (e.g., 2, 3, 4, 5, etc.), corresponding to multiple order dates. If there is only one treatment date and/or all of the separate dispensing dates have been added to the appropriate dispensing queue, the method 200 may proceed to block 222. If there are additional dispensing dates, the method 200 may return to block 210 for additional processing by the pharmacist.

At block 222, a determination is made whether all patients have been processed. For example, the pharmacist may determine if all patients on the order worklist have been processed. If all of the patients have not been processed, the method 200 may return to block 208. If all of the patients have been processed, the method 200 may end.

FIG. 3 illustrates a flow diagram of an example method 300 for improving central pharmacy-type dispensing operations according to an illustrative embodiment of the disclosure. The method 300 may begin at block 302.

At block 302, a list of patients with appointments in the current period is output. For example, the pharmacy operation module 124 may provide a pharmacist with a list of one or more patients with at least one appointment at a specific location and/or on a specific date.

At block 304, a date of service is set to apply to orders in the dispenser queue. For example, the pharmacist may create a date of service header to applicable to all orders to be added from the list to the one or more dispensing queues.

At block 306, individual patient orders are selected on the previously output list. For example, the pharmacist may select individual patients from the list and may review one or more orders associated with the patient via the worklist module 130, 156.

At block 308, a determination is made whether physical product meets order requirements. For example, the pharmacist may determine and/or select an appropriate physical medication product (e.g., medication type(s), size, medication lot, medication compositions, etc.) to fulfill the treatment order for the patient selected from the previously presented appointment list.

At block 310, medication is added to the dispensing queue for the current period. For example, the pharmacist may add the treatment order, along with any necessary corresponding patient information to one or more dispensing queues 132, 160 for the current date.

At block 312, a determination is made whether all patients have been processed. For example, the pharmacist may determine if all patients on the previously presented appointment list have been processed. If all of the patients have not been processed, the method 300 may return to block 306. If all of the patients have been processed, the method 300 may end.

FIG. 4 illustrates a flow diagram of an example method 400 for improving central pharmacy-type dispensing operations according to an illustrative embodiment of the disclosure. The method 400 may begin at block 402.

At block 402, the dispensing queue is accessed for processing. For example, the pharmacist, who may be a distinct user from the pharmacist indicated in previously illustrated embodiments and may be physically located in a separate location (e.g., medication preparation room), accesses one or more dispensing queues 132, 160 for processing.

At block 404, one or more filters are applied to obtain a desired workflow. For example, the pharmacist may apply one or more dispensing filters to the one or more dispensing queues 132, 160 obtain a suitable workflow efficiency in, for instance, a pick-and-select warehouse style or to fit a desired predefined central pharmacy-type workflow. The one or more dispensing queues 132, 160 may initially be organized by a physical location of one or more medications to minimize the instances a given secure or unsecure storage location (e.g., a door 1, a drawer A, a locker 1, etc.) is physically accessed to retrieve one or more types of medication configurations (e.g., a specific vial). Such an arrangement may not maximize the efficiency of the pharmacist and/or the dispensing of the medication. Accordingly, the pharmacist may apply one or more filters to the desired dispensing queue to obtain a suitable efficiency or otherwise faciliate a desired workflow. In some instances, the one or more dispensing filters may include, without limitation, a patient filter, one or more of a medication type filter, a treatment location filter, a date or date range filter, or any combination thereof.

At block 406, a physical medication storage location is accessed. For example, the pharmacist may access the physical medication storage location at the pharmacy location or other medication storage facility.

At block 408, the indicated medication is physically selected. For example, the pharmacist may select the one or more indicated medications located in the physical storage location.

At block 410, a determination is made whether all required orders have been processed. For example, the pharmacist may determine if all of the orders in the dispensing queue have been processed. If all of the orders have not been processed, method 400 may return to block 406. If all of the orders have been processed, the method 400 may end.

The operations described and shown in the methods 200, 300, and 400 and FIGS. 2, 3, and 4 may be carried out or performed in any suitable order as desired in various embodiments of the invention. Additionally, in certain embodiments, at least a portion of the operations may be carried out in parallel. Furthermore, in certain embodiments, fewer than or more than the operations described in FIGS. 2, 3, and 4 may be performed.

Various block and/or flow diagrams of systems, methods, apparatus, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Illustrative Graphical User Interfaces

Figure 5:
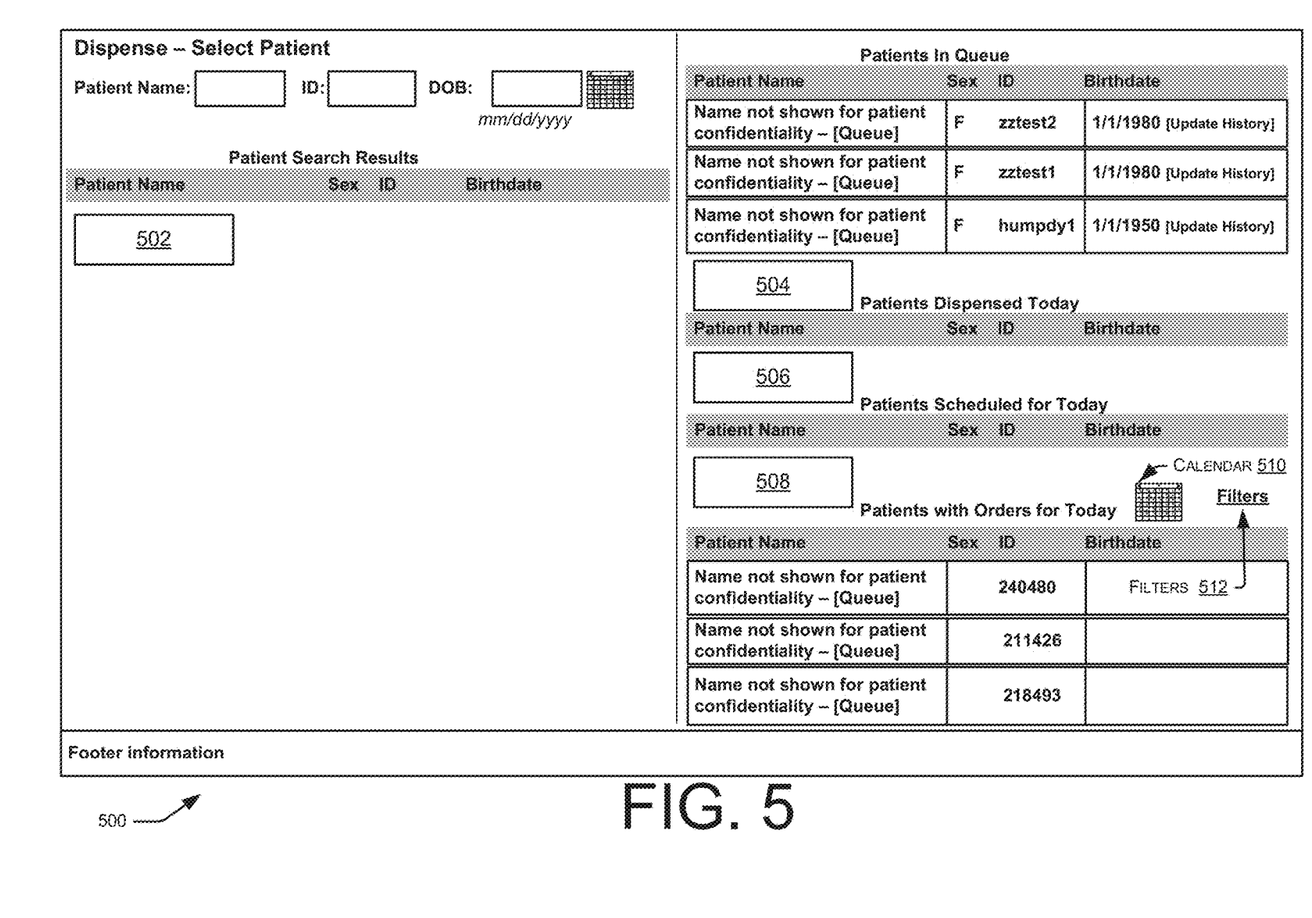
FIGS. 5-7 depict example user interfaces that may be output by example systems and methods in accordance with various embodiments of the disclosure.
Figure 6:
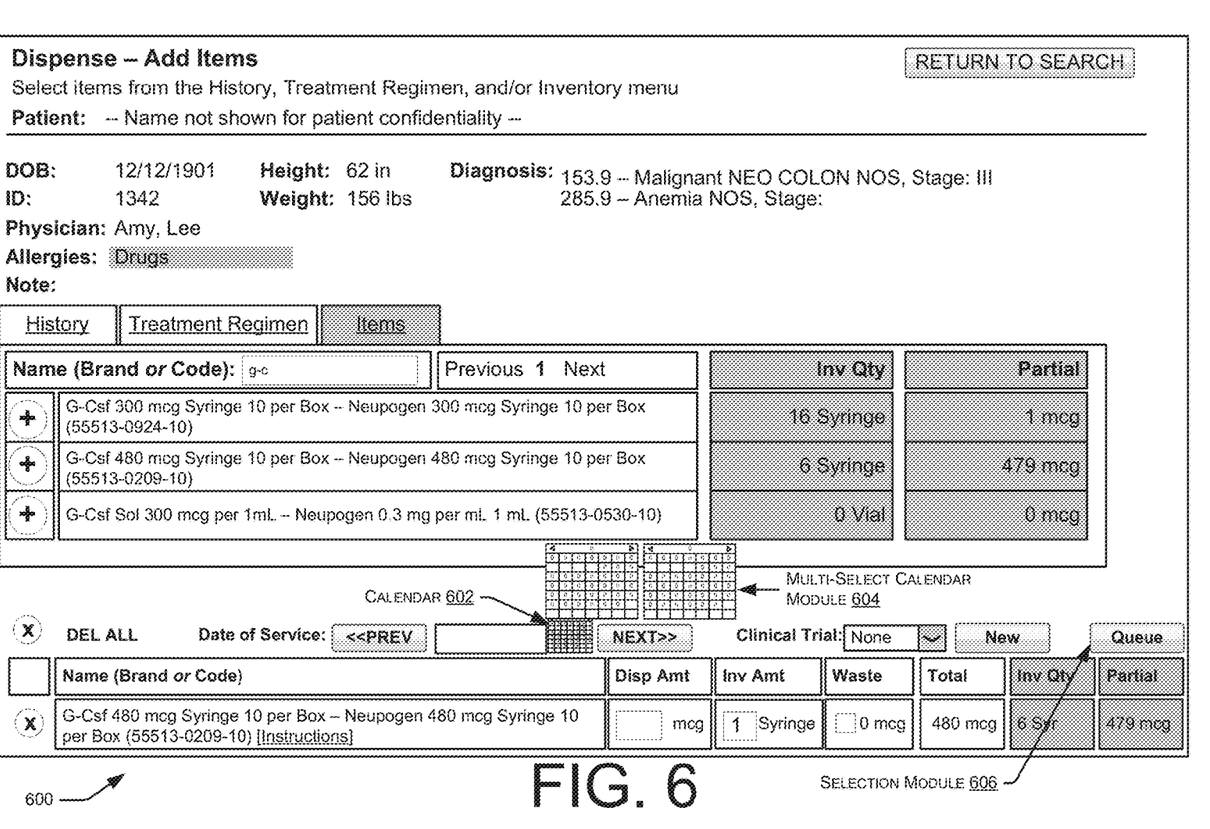
Figure 7:
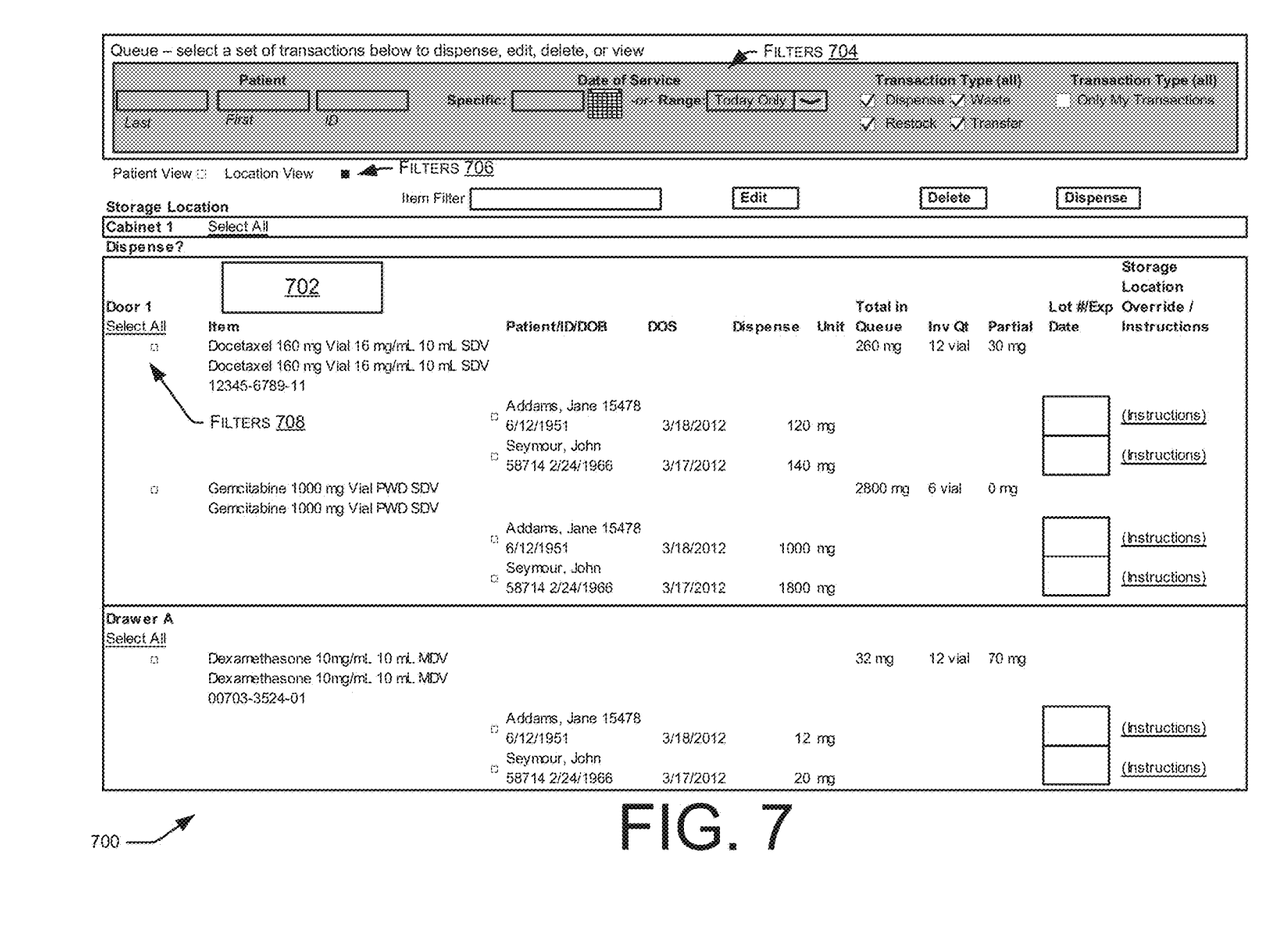

FIGS. 5-7 depict example graphical user interfaces that may be displayed in accordance with various embodiments of the disclosure. In certain embodiments, the example system of FIG. 1 and the example processes of FIGS. 2-4 can be implemented with the example graphical user interfaces. The graphical user interfaces may, for example, facilitate the collection of bulk patient information and the display of a medication order worklist generated using one or more filters applied to the bulk patient information. Additionally, in certain embodiments one or more dispensing queues 132, 160 may be generated in association with the medication order worklist.

Turning first to FIG. 5, a first example graphical user interface 500 is depicted. In one non-limiting example, the interface 500 may illustrate a filtered orders based worklist. It is to be understood, that the filtering functionality represented in FIG. 5 is a presentation of possible filtering functionality and is not intended to be an exhaustive representation. In some instances, the interface 500 may include, without limitation, one or more possible display portions 502, 504, 506 and 508. The interface 500 may also include one or more filters. In one non-limiting example, the filtering functionality may include a calendar 510 to select a date and/or a date range other than the default selection (e.g., the current date). Alternatively and/or additionally, the interface 500 may include filters 512 which may invoke a popup filter user interface (not shown). The filters 512 may also include, without limitation, a medication type filter and/or a location filter. In some instances, a single filtering criteria may be selected. Alternatively, more than one filtering criteria may be selected concurrently or sequentially.

FIG. 6 illustrates a second example graphical user interface 600 that be utilized in various embodiments of the disclosure. In one non-limiting example, the interface 600 may illustrate multiple dates of service for one patient in a dispensing queue. As shown in FIG. 6, the pharmacist may select calendar 602 to invoke a multi-select calendar module 604. The multi-select calendar module 604 may permit the pharmacist to select one or more dates for which a dispensation schedule would apply. The one or more dates may be added to a dispensation queue using a selection module 606.

FIG. 7, illustrates a second example graphical user interface 700 that be utilized in various embodiments of the disclosure. In one non-limiting example, the interface 700 may illustrate a flexible and dynamic queue format. As illustrated in interface 700, the flexible and dynamic queue format illustrates an accumulation of decisions and/or selections made by the pharmacist, as discussed above. The dispensing queue illustrated in interface 700 is an example flexible and dynamic queue format supporting a bulk-medication selection approach and thus an organization amenable to a central pharmacy model. The interface 700 may include a portion 702 that facilitates the presentation of one or more medication storage locations corresponding to one or more treatment orders associated with one or more patients. As illustrated in FIG. 7, medications may be grouped according to the physical or virtual storage location, enabling the pharmacist to open a storage location the minimum number of instances to retrieve the required amount of the medication stored in the storage location. As illustrated in FIG. 7, the flexible and dynamic queue format may include one or more filters, such as filters 704, 706 and 708. In some instances, filters 704, 706, and 708 may correspond to a medication type filter, a date or a date range filter, and/or a location filter. In one example, a single filter may be employed. Additionally and/or alternatively, more than one filter may be employed concurrently or sequentially.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments.

That which is claimed:

1. A healthcare system, comprising:
   at least one memory storing computer-executable instructions; and
   at least one processor configured to access the at least one memory and execute the computer-executable instructions, wherein the computer-executable instructions when executed by the at least one processor cause the healthcare system to:
   receive medication order data from respective electronic health records based at least in part on a user query of one or more electronic health records associated with one or more patients, wherein the query comprises at least one filter using at least one filtering criteria comprising at least one of a patient name, a date, a date range, a treatment location, or a medication;
   generate an order worklist based at least in part on the at least one filtering criteria, the order worklist comprising a plurality of medication order transactions;
   create one or more medication dispensing queues based at least in part on the order worklist, wherein a first medication dispensing queue comprises a portion of the plurality of medication order transactions, and wherein each of the plurality of medication order transaction comprises a request for one or more medications to be dispensed by a pharmacy;
   apply a first filter to the portion of the plurality of medication order transactions in the first medication dispensing queue, wherein the portion of the plurality of medication order transactions are filtered based on at least one of the following: medication type, treatment location, a date, or a date range;
   apply a location filter to the filtered portion of the plurality of medication order transactions in the first medication dispensing queue, wherein the filtered portion of the plurality of medication order transactions are ordered within the first medication queue corresponding to a respective physical storage location of a respective medication within the pharmacy, and wherein the location filter facilitates determining a minimum number of instances the respective physical storage location needs to be accessed to retrieve a predefined amount of the respective medication to fulfill the filtered portion of the plurality of medication order transactions; and
   facilitate output of a representation of the filtered portion of the plurality of medication order transactions in the first medication dispensing queue for presentation to the pharmacy via a graphical user interface, wherein the filtered portion of the plurality of medication order transactions in the first medication dispensing queue are filled by the pharmacy using a desired workflow to obtain the respective medication from the respective first physical storage location using the minimum number of instances the respective physical storage location needs to be accessed to retrieve the predefined amount of the respective medication to fulfill the filtered portion of the plurality of medication order transactions.

2. The system of claim 1, wherein the order worklist is generated by applying one or more filters to the medication order data associated with the one or more patients.

3. The system of claim 1, wherein two or more of the at least one filtering criteria are applied concurrently or sequentially.

4. The system of claim 1, wherein the computer-executable instructions when executed by the at least one processor further cause the healthcare system to:
   apply one or more additional dispensing filters to the filtered portion of the plurality of medication order transactions in the first medication dispensing queue, the one or more additional dispensing filters comprising at least one of a vial type filter or a medication type filter.

5. The system of claim 1, wherein the computer-executable instructions when executed by the at least one processor further cause the healthcare system to:
   process two or more dispensing dates to result in two or more corresponding date entries in the first medication dispensing queue.

6. The system of claim 1, wherein the first medication dispensing queue is generated on a first calendar date and assigned to a dispense date of service corresponding to a second calendar date.

7. A computer-implemented method comprising;
receiving, by a healthcare system comprising one or more computers, medication order data associated with the one or more patients, wherein the medication order data is received based at least in part on a user query of one or more electronic health records associated with one or more patients, wherein the query comprises at least one filter using at least one filtering criteria comprising at least one of a patient name, a date, a date range, a treatment location, or a medication,;
generating, by the healthcare system, an order worklist based at least in part on the at least one filtering criteria, the order worklist comprising a plurality of medication order transactions;
creating one or more medication dispensing queues based at least in part on the order worklist, wherein a first medication dispensing queue comprises a portion of the plurality of medication order transactions, and wherein each of the plurality of medication order transactions comprises a request for one or more medications to be dispensed by a pharmacy;
applying a first filter to the portion of the plurality of medication order transactions in first medication dispensing queue, wherein the portion of the plurality of medication order transactions are filtered based on at least one of the following: medication type, treatment location, a date, or a date range;
applying a location filter to the filtered portion of the plurality of medication order transactions in the first medication dispensing queue, wherein the filtered portion of the plurality of medication order transactions are ordered within the first medication queue corresponding to a respective physical storage location of a respective medication within the pharmacy, and wherein the location filter facilitates determining a minimum number of instances the respective physical storage location needs to be accessed to retrieve a predefined amount of the respective medication to fulfill the filtered portion of the plurality of medication order transactions; and
facilitating, by the healthcare system, output of a representation of the filtered portion of the plurality of medication order transactions in the first medication dispensing queue for presentation to the pharmacy via a graphical user interface, wherein the filtered portion of the plurality of medication order transactions in the first medication dispensing queue are filled by the pharmacy using a desired workflow to obtain the respective first medication from the respective first physical storage location using the minimum number of instances the respective physical storage location needs to be accessed to retrieve the predefined amount of the respective medication to fulfill the filtered portion of the plurality of medication order transactions.

8. The computer-implemented method of claim 7, wherein the order worklist is generated by applying one or more filters to the medication order data associated with the one or more patients.

9. The computer-implemented method of claim 7, wherein at least two or more of the at least one filtering criteria are applied concurrently or sequentially.

10. The computer-implemented method of claim 7, further comprising:
applying one or more dispensing filters to the filtered portion of the plurality of medication order transactions in the first medication dispensing queue, the one or more dispensing filters comprising at least one of a vial type filter or a medication type filter.

11. The computer-implemented method of claim 7, wherein the first medication dispensing queue is generated on a first calendar date and assigned to a dispense date of service corresponding to a second calendar date.

12. The computer-implemented method of claim 7, further comprising:
processing two or more dispensing dates to result in two or more corresponding date entries in the first medication dispensing queue.

* * * * *